United States Patent
Fang et al.

(10) Patent No.: US 11,008,552 B2
(45) Date of Patent: May 18, 2021

(54) MULTICOPPER OXIDASE MUTANT WITH IMPROVED SALT TOLERANCE

(71) Applicant: Jiangnan University, Wuxi (CN)

(72) Inventors: Fang Fang, Wuxi (CN); Tao Yang, Wuxi (CN); Jingwen Zhou, Wuxi (CN); Jian Chen, Wuxi (CN); Guocheng Du, Wuxi (CN); Jie Xu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/524,382

(22) Filed: Jul. 29, 2019

(65) Prior Publication Data

US 2019/0382735 A1    Dec. 19, 2019

(30) Foreign Application Priority Data

May 24, 2019  (CN) .......................... 201910440487.8

(51) Int. Cl.
*C12N 9/02* (2006.01)
*C12N 15/52* (2006.01)
*A23L 5/20* (2016.01)

(52) U.S. Cl.
CPC .............. *C12N 9/0004* (2013.01); *A23L 5/25* (2016.08); *C12N 15/52* (2013.01)

(58) Field of Classification Search
None
See application file for complete search history.

(56) References Cited

PUBLICATIONS

Q. Lou et al. "Functional expression enhancement of Bacillus pumilus CotA-laccase mutant WLF through site-directed mutagenesis", Enzyme and Microbial Technology 109: 11-19 (Year: 2018).*
P. Durao et al. "Proximal mutations at the type 1 copper site of CotA laccase: spectroscopic, redox, kinetic and structural characterization of I494A and L386A mutants", Biochem. J. 412: 339-346 (Year: 2008).*
B. Chen "A novel non-blue laccase from Bacillus amyloliquefaciens: Secretory expression and characterization", International Journal of Biological Macromolecules 76: 39-44 (Year: 2015).*
S. Brander et al. "Characterization of an Alkali- and Halide-Resistant Laccase Expressed in *E. coli*: CotA from Bacillus clausii", PLOS ONE 9(6): 1-II, e99402 (Year: 2014).*

* cited by examiner

*Primary Examiner* — Rebecca E Prouty
(74) *Attorney, Agent, or Firm* — IPro, PLLC

(57) ABSTRACT

The present disclosure provides a multicopper oxidase mutant with improved salt tolerance. Threonine at site 317 of wild-type multicopper oxidase WT was mutated to asparagine, leucine at site 386 was mutated to tyrosine, and serine at site 427 was mutated to glutamic acid by site-directed mutagenesis to obtain a mutant T317N-L386Y-S427E. Compared with WT, the tolerance of T317N-L386Y-S427E to 6%, 9%, 12%, 15% and 18% NaCl (W/V) is improved.

5 Claims, 2 Drawing Sheets

Specification includes a Sequence Listing.

SEQUENCE LISTING

<160> NUMBER OF SEQ ID NOS: 12

<210> SEQ ID NO 1
<211> LENGTH: 518
<212> TYPE: PRT
<213> ORGANISM: Artificial Sequence
<220> FEATURE:
<223> OTHER INFORMATION: Protein translated from synthetic DNA

<400> SEQUENCE: 1

```
Met Ala Leu Glu Lys Phe Ala Asp Glu Leu Pro Ile Ile Glu Thr Leu
1               5                   10                  15

Lys Pro Gln Lys Thr Ser Asn Gly Ser Thr Tyr Tyr Glu Val Thr Met
            20                  25                  30

Lys Glu Cys Phe His Lys Leu His Arg Asp Leu Pro Pro Thr Arg Leu
        35                  40                  45

Trp Gly Tyr Asn Gly Leu Phe Pro Gly Pro Thr Ile Asp Val Asn Gln
    50                  55                  60

Asp Glu Asn Val Tyr Ile Lys Trp Met Asn Asp Leu Pro Asp Lys His
65                  70                  75                  80

Phe Leu Pro Val Asp His Thr Ile His His Ser Glu Gly Gly His Gln
                85                  90                  95

Glu Pro Asp Val Lys Thr Val Val His Leu His Gly Gly Ala Thr Pro
            100                 105                 110

Pro Asp Ser Asp Gly Tyr Pro Glu Ala Trp Phe Thr Arg Asp Phe Lys
        115                 120                 125

Glu Lys Gly Pro Tyr Phe Lys Lys Glu Val Tyr His Tyr Pro Asn Lys
    130                 135                 140

Gln Arg Gly Ala Leu Leu Trp Tyr His Asp His Ala Met Ala Ile Thr
145                 150                 155                 160

Arg Leu Asn Val Tyr Ala Gly Leu Ala Gly Met Tyr Ile Ile Arg Glu
                165                 170                 175

Arg Lys Glu Lys Gln Leu Lys Leu Pro Ala Gly Glu Tyr Asp Val Pro
            180                 185                 190

Leu Met Ile Met Asp Arg Thr Leu Asn Asp Asp Gly Ser Leu Phe Tyr
        195                 200                 205

Pro Ser Gly Pro Asp Asn Pro Ser Glu Thr Leu Pro Asn Pro Ser Ile
    210                 215                 220

Val Pro Phe Leu Cys Gly Asn Thr Ile Leu Val Asn Gly Lys Ala Trp
225                 230                 235                 240

Pro Tyr Met Glu Val Glu Pro Arg Thr Tyr Arg Phe Arg Ile Leu Asn
                245                 250                 255

Ala Ser Asn Thr Arg Thr Phe Ser Leu Ser Leu Asn Asn Gly Gly Arg
            260                 265                 270

Phe Ile Gln Ile Gly Ser Asp Gly Gly Leu Leu Pro Arg Ser Val Lys
        275                 280                 285
```

Thr Gln Ser Ile Ser Leu Ala Pro Ala Glu Arg Tyr Asp Val Leu Ile
    290                 295                 300

Asp Phe Ser Ala Phe Asp Gly Glu His Ile Ile Leu Asn Asn Gly Thr
305                 310                 315                 320

Gly Cys Gly Gly Asp Val Asn Pro Asp Thr Asp Ala Asn Val Met Gln
                325                 330                 335

Phe Arg Val Thr Lys Pro Leu Lys Gly Glu Asp Thr Ser Arg Lys Pro
            340                 345                 350

Lys Tyr Leu Ser Ala Met Pro Asp Met Thr Ser Lys Arg Ile His Asn
        355                 360                 365

Ile Arg Thr Leu Lys Leu Thr Asn Thr Gln Asp Lys Tyr Gly Arg Pro
    370                 375                 380

Val Tyr Thr Leu Asn Asn Lys Arg Trp His Asp Pro Val Thr Glu Ala
385                 390                 395                 400

Pro Arg Leu Gly Ser Thr Glu Ile Trp Ser Ile Ile Asn Pro Thr Arg
                405                 410                 415

Gly Thr His Pro Ile His Leu His Leu Val Glu Phe Gln Val Leu Asp
            420                 425                 430

Arg Arg Pro Phe Asp Leu Glu Arg Tyr Asn Lys Phe Gly Asp Ile Val
        435                 440                 445

Tyr Thr Gly Pro Ala Val Pro Pro Pro Ser Glu Lys Gly Trp Lys
    450                 455                 460

Asp Thr Val Gln Ala His Ser Gly Glu Val Ile Arg Ile Ala Ala Thr
465                 470                 475                 480

Phe Ala Pro Tyr Ser Gly Arg Tyr Val Trp His Cys His Ile Leu Glu
                485                 490                 495

His Glu Asp Tyr Asp Met Met Arg Pro Met Asp Val Thr Glu Lys Gln
            500                 505                 510

His His His His His His
        515

<210> SEQ ID NO 2
<211> LENGTH: 1557
<212> TYPE: DNA
<213> ORGANISM: Artificial Sequence
<220> FEATURE:
<223> OTHER INFORMATION: Synthetic DNA

<400> SEQUENCE: 2

```
atggcacttg aaaaatttgc agatgaactg ccgattatcg aaacactgaa gccgcagaag      60
acatcaaacg gcagcacgta ttatgaagtc acgatgaagg aatgctttca caagctgcac     120
cgtgatctcc cgccgacccg gctgtgggga tataacggtt tgtttcccgg cccgacgatt     180
gatgtgaacc aagatgaaaa cgtctatatt aaatggatga atgacctgcc ggataagcat     240
tttctccctg tggaccatac cattcaccat tcagagggcg ccatcagga accccgacgtc     300 aaaactgtcg tccatttaca cggaggagca acgccgccgg acagcgacgg ctatccggaa     360
gcctggttca cacgggattt caaggagaag gggccttatt taaaaaaga ggtataccac     420 tatccaaaca aacagcgcgg ggcgctatta tggtatcacg accacgccat ggcaattacg     480
aggctcaatg tgtacgccgg gcttgccggc atgtatatca tccgcgagcg aaaagaaaag     540
cagctgaagc ttcccgccgg agaatacgac gtaccgctta tgattatgga ccgcacgtta     600
aatgacgacg gttccttgtt ttatccgagc gggcccgata tccttccga aacgctgccg     660 aatccttcaa tcgttccgtt tctttgcgga aataccattc tcgtcaacgg caaagcgtgg     720
```

```
ccgtatatgg aagtcgaacc gcggacatat cgtttccgta tccttaacgc tcaaatacg    780 agaacatttt ctctctcgct caataatggc ggccggttta tccaaatcgg ttcagacggc    840
ggactgctcc cccgttctgt caaaacacag tccatcagct tagcaccggc tgagcggtat    900
gatgtgctca ttgatttctc cgcttttgac ggagaacata ttatttttaaa caacggcacc   960 ggctgcgggg gcgacgtcaa tccggatacc gacgccaatg tgatgcaatt ccgcgtcaca   1020
aaaccgctga agggagaaga caccagccgg aagcctaaat atctgtcagc catgcctgat   1080
atgacatcaa aaagaataca caatatcagg acgcttaaac tcacaaacac gcaagacaaa   1140
tacggccggc cggtttatac gctcaataac aagcgctggc atgatcccgt gacagaagcg   1200
ccgcggctcg gctcaacgga aatctggtcg attatcaatc cgacgcgggg aacccatccg   1260
atacacctgc acttggttga gttccaagtc cttgaccggc gtccttttga cttgaaacgt   1320
tataacaaat tcggcgacat tgtgtataca ggccccgccg tcccgccgcc tccaagtgaa   1380
aaaggctgga agacaccgt gcaggcgcac tccggagaag tcatcagaat cgcggcgaca   1440 ttcgccccctt acagcggacg gtacgtatgg cattgtcata ttttagaaca cgaagattat   1500
gacatgatga gaccgatgga cgtcacagaa aagcagcatc atcaccacca ccactaa     1557
```

```
<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
ttttaaacaa cggcaccggc tg                                              22

<210> SEQ ID NO 4
<211> LENGTH: 30
<212> TYPE: DNA
<213> ORGANISM: Artificial Sequence
<220> FEATURE:
<223> OTHER INFORMATION: Synthetic DNA

<400> SEQUENCE: 4
gtgccgttgt ttaaaataat atgttctccg                                      30

<210> SEQ ID NO 5
<211> LENGTH: 26
<212> TYPE: DNA
<213> ORGANISM: Artificial Sequence
<220> FEATURE:
<223> OTHER INFORMATION: Synthetic DNA

<400> SEQUENCE: 5
gccggtttat acgctcaata acaagc                                          26

<210> SEQ ID NO 6
<211> LENGTH: 25
<212> TYPE: DNA
<213> ORGANISM: Artificial Sequence
<220> FEATURE:
<223> OTHER INFORMATION: Synthetic DNA

<400> SEQUENCE: 6
gttattgagc gtataaaccg gccgg                                           25

<210> SEQ ID NO 7
```

```
<211> LENGTH: 36
<212> TYPE: DNA
<213> ORGANISM: Artificial Sequence
<220> FEATURE:
<223> OTHER INFORMATION: Synthetic DNA

<400> SEQUENCE: 7
cacctgcact tggttgagtt ccaagtcctt gaccgg                               36

<210> SEQ ID NO 8
<211> LENGTH: 37
<212> TYPE: DNA
<213> ORGANISM: Artificial Sequence
<220> FEATURE:
<223> OTHER INFORMATION: Synthetic DNA

<400> SEQUENCE: 8
caaggacttg gaactcaacc aagtgcaggt gtatcgg                              37

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9
ttacacggag gagaaacgcc g                                               21

<210> SEQ ID NO 10
<211> LENGTH: 24
<212> TYPE: DNA
<213> ORGANISM: Artificial Sequence
<220> FEATURE:
<223> OTHER INFORMATION: Synthetic DNA

<400> SEQUENCE: 10
gtttctcctc cgtgtaaatg gacg                                            24

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
ttacacggag gagaaacgcc g                                               21

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA

<400> SEQUENCE: 12
gtttctcctc cgtgtaaatg gacg                                            24
```

MULTICOPPER OXIDASE MUTANT WITH IMPROVED SALT TOLERANCE

The disclosure herein relates to a multicopper oxidase mutant with improved salt tolerance, more particularly relates to a multicopper oxidase mutant with improved salt tolerance derived from *Bacillus amyloliquefaciens*, and belongs to the technical field of bioengineering.

BACKGROUND

Biogenic amines are a general term for low molecular weight nitrogen-containing organic compounds, which are normal physiologically active substances in living organisms. The proper amount of biogenic amines synthesized by the human body help to maintain the normal physiological function of the body. However, when excessive biogenic amines are taken through food, they can cause allergic reactions such as headaches, nausea, palpitations, blood pressure changes and respiratory disorders, and they can threaten life in serious cases.

The biogenic amines are widely found in fermented foods rich in protein content such as aquatic products, meat products and seasonings, as well as alcoholic fermented beverages. Few biogenic amines in the fermented food are from the raw materials, and most of biogenic amines in the fermented food are formed by decarboxylation of amino acids. In addition to the biogenic amines contained in the food itself, most of the biogenic amines in the fermented food are formed by amino decarboxylation. The abundant protein in food is decomposed into amino acids under the co-action of endopeptidase and exopeptidase, and the amino acid is oxidized to produce the biogenic amines under the catalysis of the corresponding amino acid decarboxylase. The common biogenic amines in the food include putrescine, cadaverine, spermine, spermidine, tyramine, phenethylamine and histamine. The most toxic biogenic amine is histamine, followed by tyramine.

With the improvement of living standards, people's requirements for food safety are getting higher and higher, and the harm of potential toxic effects of the biogenic amines to human health should not be underestimated. Therefore, effective measures should be taken to control and reduce biogenic amine content in food mainly starts from three aspects: (1) Control from the source: (1.1) most of the biogenic amines in food are formed by amino decarboxylation, therefore, the content of free amino acid can be controlled to reduce the content of biogenic amines. However, the free amino acid in food is mainly a hydrolysis product of protein in a raw material. Controlling the content of free amino acid means reducing the protein content, which will affect the flavor of some high-protein foods; (1.2) the strain with no amino acid decarboxylase activity is used to replace the original production strain and is added to a fermentation system at the beginning of fermentation. However, due to the great variety and complex relationship of the original production strains for mixed fermentation and open fermentation, replacing one kind of the strains may cause a change in the entire fermentation system, thereby ultimately resulting in fermentation failure, so this type of control is generally only applicable to a closed single-strain fermentation system. (2) Process control: (2.1) the growth of biogenic amine-producing bacteria is inhibited by rational selection of raw materials, temperature and salinity in the production process so as to achieve the purpose of inhibiting the production of biogenic amines; the limitation of this method lies in that the factors such as processing temperature and salinity are mostly determined by food characteristics, while low temperature storage will increase equipment and energy consumption costs, and some microorganisms can produce biogenic amines at a low temperature; (2.2) strains that degrade biogenic amines are added in the fermentation process to degrade the biogenic amines produced in the fermentation process without affecting dominant strains for production in the fermentation system, the limitation of this method lies in that there is concern about the safety of the added strains and the flavors of the food may be affected. (3) Terminal elimination: the biogenic amines already formed in the food are degraded by adding biogenic amine degrading enzymes to fermented foods, this method does not substantially affect the production process of the fermented foods, and has little effect on food nutrition and flavor, so the method is currently the most promising method.

Regarding the biogenic amine degrading enzymes, researchers have attempted to isolate and purify enzymes capable of degrading biogenic amines from screened strains capable of degrading biogenic amines, and to preliminarily analyze the action mechanism of the enzymes. Amine oxidase, amine dehydrogenase and multicopper oxidase are currently the three main types of enzymes capable of degrading biogenic amines. Amine oxidase and histamine dehydrogenase capable of degrading biogenic amines can only specifically act on certain biogenic amine or certain biogenic amines, and the activity is also inhibited by ethanol or carbonyl compounds, and the optimum pH of the enzyme is mostly neutral at the same time, therefore, it is difficult to achieve the desired results when using these two types of enzymes to degrade the biogenic amines in alcohol-containing fermented beverages and acidic fermented foods. The multicopper oxidase can catalyze various biogenic amines to oxidize to generate corresponding aldehydes, ammonia and water, the activity is less affected by an acidic environment and ethanol, but a high salt environment in high-salt fermented food (such as soy sauce containing 18% salt) will quickly inactivate the enzyme and affect the degradation effect of the enzyme on the biogenic amines. Therefore, the improvement on the salt tolerance of multicopper oxidase is of great significance for establishing an enzymatic reduction and control method for biogenic amines in the fermented food.

SUMMARY

The technical problem to be solved by the present invention is to provide a multicopper oxidase mutant with improved salt tolerance and a preparation method thereof. The salt tolerance refers to the tolerance ability of multicopper oxidase to NaCl, and the improved salt tolerance refers to the improved tolerance ability of multicopper oxidase to NaCl.

The present invention provides a multicopper oxidase mutant with improved salt tolerance. The mutant is a mutant T317N-L386Y-S427E obtained by mutating threonine at site 317 of *B. amyloliquefaciens* multicopper oxidase into asparagine, mutating leucine at site 386 into tyrosine and mutating serine at site 427 into glutamic acid. The amino acid sequence of the multicopper oxidase mutant is as shown in SEQ ID NO:1.

The nucleotide sequence of a gene encoding the multicopper oxidase mutant is as shown in SEQ ID NO:2.

The present invention also provides a method for preparing the multicopper oxidase mutant with improved salt tolerance as described above, comprising the following steps:

(1) determining a mutation site based on the amino acid sequence of the multicopper oxidase of *B. amyloliquefaciens*; designing site-directed mutagenesis primers to carry out site-directed mutagenesis by using a vector carrying the gene encoding the multicopper oxidase of *B. amyloliquefaciens* as a template, and constructing to obtain a plasmid vector containing the gene encoding the mutant;

(2) transforming the mutant plasmid into a host cell;

(3) selecting positive clones for fermentation culture and purifying to obtain the multicopper oxidase mutant.

According to the present invention, the multicopper oxidase derived from *B. amyloliquefaciens* is modified, so that the tolerance of the mutant T317N-L386Y-S427E in different concentrations (6%, 9%, 12%, 15% and 18% (W/V)) of NaCl is improved, and the relative activity is increased by 15% or more compared with the unmutated multicopper oxidase (WT). The multicopper oxidase mutant T317N-L386Y-S427E with improved salt tolerance can be used to degrade biogenic amines in high-salt fermented food such as soy sauce, fermented sausages and bacon.

DETAILED DESCRIPTION

Figure 1:
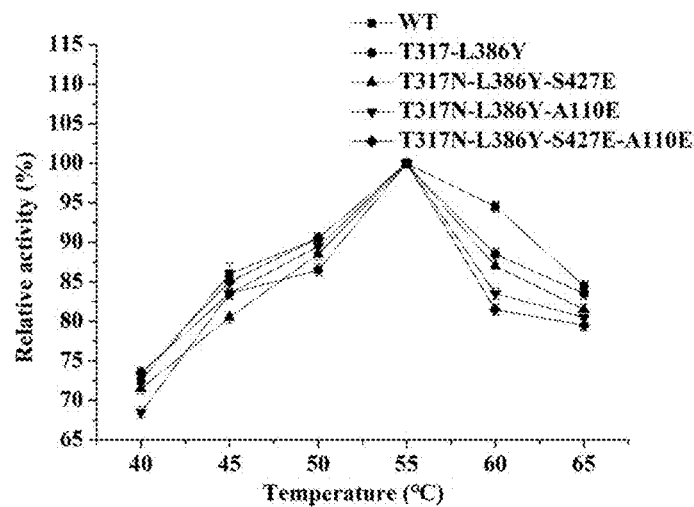
FIG. 1 shows effects of different temperatures on activities of unmutated multicopper oxidase (WT) and mutants.
Figure 2:
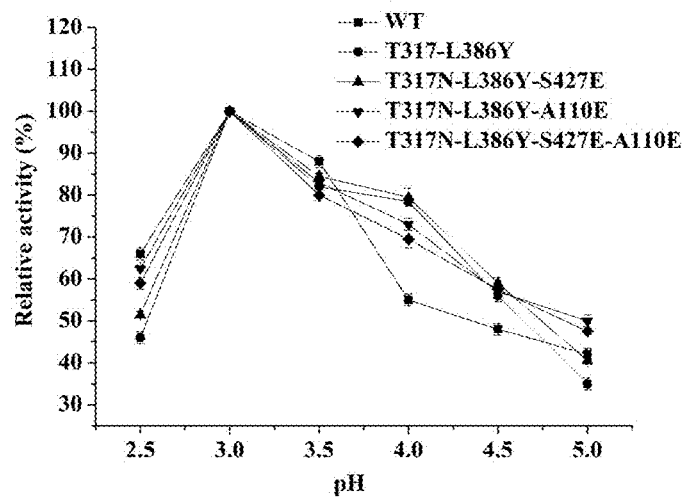
FIG. 2 shows effects of different pH on activities of the unmutated multicopper oxidase (WT) and mutants.
Figure 3:
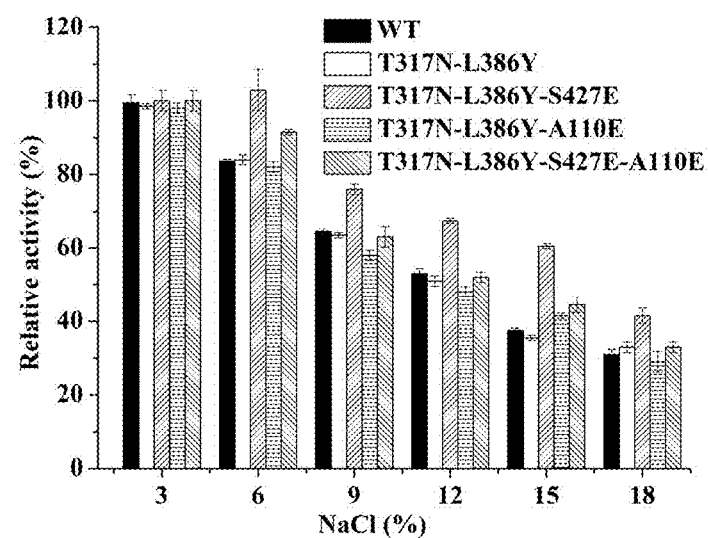
FIG. 3 shows effects of different concentrations of NaCl (W/V) on activities of the unmutated multicopper oxidase (WT) and the mutant.

PrimerSTAR DNA polymerase and Solution I DNA ligase were purchased from TaKaRa Company (Dalian); EcoR I, Hind III, DpnI rapid restriction enzymes and DNA recovery kits were purchased from Thermo Fisher Scientific Company (USA); plasmid extraction kits and kanamycin were purchased from Sangon Biotech (Shanghai) Co., Ltd.; ABTS was purchased from aladdin Company. All other reagents are analytically pure reagents.

Reaction system and method for determining activity of multicopper oxidase:

The activity of multicopper oxidase was determined by a visible light absorptiometry: by using ABTS as a substrate, the activity of the multicopper oxidase was calculated by detecting the absorbance of reaction system after the enzyme reacting with the substrate for 2 min by using a reaction kinetics instrument. The reaction system includes 100 μL of an enzyme solution, 2900 μL of a citric acid-sodium citrate buffer (the citric acid-sodium citrate buffer contains 0.5 mM of ABTS and 1 mM of $CuCl_2$). The reaction temperature and pH adopt the optimum temperature and optimum pH of the enzyme. The amount of enzyme required to catalyze 1 μmol of substrate per minute to oxidize is defined as an activity unit (U).

$$\text{Enzyme activity}(U/L) = \frac{\Delta OD \times V_1}{\Delta t \times V_2 \times \varepsilon \times 10^{-6}}$$

where:

$\varepsilon$: Molar absorptivity of ABTS at 420 nm, $\varepsilon = 3.6 \times 10^4 \text{ M}^{-1} \text{ cm}^{-1}$ $\Delta t$: 2 min;

DOD: Change value of absorbance $OD_{420}$ within 2 min;

V1: Total volume of a reaction solution in an enzyme reaction system, that is, 3 mL;

V2: Volume of an enzyme solution in the enzyme reaction system, that is, 100 μL.

Example 1: Construction of Recombinant Bacteria

A plasmid pET28a(+) carrying a T7 promoter was selected as an expression vector, and the pET28a(+) plasmid and an mcob gene, obtained by amplifying, encoding the unmutated multicopper oxidase were separately subjected to EcoR I and Hind III double enzyme digestion, the digested product was subjected to gel extraction, and then ligated with the DNA ligase Solution I overnight, the ligated product was transformed into *E. coli* JM109 competent cells, and cultured at 37° C. for 10 h, and positive transformants were identified by colony PCR.

Three positive transformants were picked and inoculated in LB broth (containing 50 μg/mlkanamycin), and cultured at 37° C. for 10 h, and the plasmid was extracted to be validated by sequencing. The plasmid pET28a(+)-MCOB with correct sequence was transformed into *E. coli* BL21 (DE3), and then plated on LB agar containing 50 μg/mlkanamycin, and cultured at 37° C. for 10 h. Single colonies of transformants were picked, named BL21(DE3)-pET28a(+)-MCOB and inoculated in LB broth containing 50 μg/mlkanamycin, and cultured at 37° C. for 10 h, and the bacterial culture was mixed with sterile glycerol and stored at −80° C. The multicopper oxidase expressed by BL21(DE3)-pET28a(+)-MCOB was named as WT.

Example 2: Preparation of Mutant T317N-L386Y (1) Preparation of Mutant T317N

According to the gene sequence of multicopper oxidase of *B. amyloliquefaciens*, primers for introducing T317N mutation were designed and synthesized, and an expression vector pET28a(+)-MCOB was used as a template by a rapid PCR technology.

Primers for introducing the T317N mutation by site-directed mutagenesis were:

SEQ. ID NO: 3: Forward primer:
5'-TTTTA<u>AAC</u>AACGGCACCGGCTG-3' (the underline represents a mutated base)

SEQ. ID NO: 4: Reverse primer:
5'-GTGCCGTT<u>GTT</u>TAAAATAATATGTTCTCCG-3' (the underline represents a mutated base)

PCR reaction system: 25 μL of 2× PrimerSTAR DNA polymerase, 1 μL of forward primer (10 μM), 1 μL of reverse primer (10 μM), 1 μL of template DNA, and 22 μL of $ddH_2O$.

PCR amplification conditions: pre-denature at a temperature of 95° C. for 3 min; followed by 30 cycles (95° C. 30 s, 55° C. 30 s, and 72° C. 7 min); supplement and extend at a temperature of 72° C. for 10 min.

The PCR product was digested with DpnI and transformed into the *E. coli* BL21(DE3) competent cells. Monoclones were selected for sequencing. A strain with correct sequencing results was mixed with sterile glycerol and stored at −80° C. The strain was named BL21(DE3)-pET28a (+)-T317N. The multicopper oxidase mutant expressed by this strain was named T317N.

(2) Preparation of Mutant T317N-L386Y

According to the gene sequence of multicopper oxidase of *B. amyloliquefaciens*, primers introducing L386Y mutation were designed and synthesized, and a vector carrying a gene encoding the mutant T317N was used as a template by a rapid PCR technology.

Site-directed mutagenesis primers introducing the L386Y mutation were:

```
SEQ. ID NO: 5: Forward primer:
5'-GCCGGTTTATACGCTCAATAACAAGC-3'(the underline represents a mutated base)

SEQ. ID NO: 6: Reverse primer:
5'-GTTATTGAGCGTATAAACCGGCCGG-3'(the underline represents a mutated base)
```

PCR reaction system: 25 µL of 2× PrimerSTAR DNA polymerase, 1 µL of forward primer (10 µM), 1 µL of reverse primer (10 µM), 1 µL of template DNA 1 µL, and 22 µL of ddH$_2$O.

PCR amplification conditions: pre-denature at 95° C. for 3 min; followed by 30 cycles (95° C. 30 s, 55° C. 30 s, and 72° C. 7 min); supplement and extend at 72° C. for 10 min.

The PCR product was digested with DpnI and transformed into the *E. coli* BL21(DE3) competent cells. Monoclones were selected for sequencing. A strain with correct sequencing results was mixed with sterile glycerol and stored at −80° C. The strain was named BL21(DE3)-pET28a (+)-T317N-L386Y. The multicopper oxidase mutant expressed by this strain was named T317N-L386Y.

Example 3: Preparation of Mutant
T317N-L386Y-S427E and T317N-L386Y-A110E (1) Preparation of Mutant T317N-L386Y-S427E According to the gene sequence of multicopper oxidase of *B. amyloliquefaciens*, primers introducing S427E mutation were designed and synthesized, and a vector carrying a gene encoding the mutant T317N-L386Y was used as a template by a rapid PCR technology.

Site-directed mutagenesis primers introducing the S427E mutation were:

```
SEQ. ID NO: 7: Forward primer:
5'-CACCTGCACTTGGTTGAGTTCCAAGTCCTTGACCGG-3'(the underline represents a mutated base)

SEQ. ID NO: 8: Reverse primer:
5'-CAAGGACTTGGAACTCAACCAAGTGCAGGTGTATCGG-3'(the underline represents a mutated base)
```

PCR reaction system: 25 µL of 2× PrimerSTAR DNA polymerase, 1 µL of forward primer (10 µM), 1 µL of reverse primer (10 µM), 1 µL of template DNA, and 22 µL of ddH$_2$O.

PCR amplification conditions: pre-denature at 95° C. for 3 min; followed by 30 cycles (95° C. 30 s, 55° C. 30 s, and 72° C. 7 min); supplement and extend at 72° C. for 10 min.

The PCR product was digested with DpnI and transformed into the *E. coli* BL21(DE3) competent cells. Monoclones were selected and sent to Shanghai Sangon Biotech for sequencing. A strain with correct sequencing results was mixed with sterile glycerol and stored at −80° C. The strain was named BL21(DE3)-pET28a(+)-T317N-L386Y-S427E. The multicopper oxidase mutant expressed by this strain was named T317N-L386Y-S427E.

(2) Preparation of Mutant T317N-L386Y-A110E

According to the gene sequence of multicopper oxidase of *B. amyloliquefaciens*, primers introducing A110E mutation were designed and synthesized, and a vector carrying a gene encoding the mutant T317N-L386Y was used as a template by a rapid PCR technology.

Site-directed mutagenesis primers introducing the A110E mutation were:

```
SEQ. ID NO: 9: Forward primer:
5'- TTACACGGAGGAGAAACGCCG -3'(the underline represents a mutated base)

SEQ. ID NO: 10: Reverse primer:
5'- GTTTCTCCTCCGTGTAAATGGACG -3'(the underline represents a mutated base)
```

PCR reaction system: 25 µL of 2× PrimerSTAR DNA polymerase, 1 µL of forward primer (10 µM), 1 µL of reverse primer (10 µM), 1 µL of template DNA, and 22 µL of ddH$_2$O.

PCR amplification conditions: pre-denature at 95° C. for 3 min; followed by 30 cycles (95° C. 30 s, 55° C. 30 s, and 72° C. 7 min); supplement and extend at 72° C. for 10 min.

The PCR product was digested with DpnI and transformed into the *E. coli* BL21(DE3) competent cells. Monoclones were selected and sent to Shanghai Sangon Biotech for sequencing. A strain with correct sequencing results was mixed with sterile glycerol and stored at −80° C. The strain was named BL21(DE3)-pET28a(+)-T317N-L386Y-A110E. The multicopper oxidase mutant expressed by this strain was named T317N-L386Y-A110E.

Example 4: Preparation of Mutant
T317N-L386Y-S427E-A110E

According to the gene sequence of multicopper oxidase of *B. amyloliquefaciens*, primers introducing A110E mutation were designed and synthesized, and a vector carrying a gene encoding the mutant T317N-L386Y-S427E was used as a template by a rapid PCR technology.

Site-directed mutagenesis primers introducing the A110E mutation were:

```
SEQ. ID NO: 11: Forward primer:
5'- TTACACGGAGGAGAAACGCCG -3'(the underline represents a mutated base)

SEQ. ID NO: 12: Reverse primer:
5'- GTTTCTCCTCCGTGTAAATGGACG -3'(the underline represents a mutated base)
```

PCR reaction system: 25 µL of 2× PrimerSTAR DNA polymerase, 1 µL of forward primer (10 µM), 1 µL of reverse primer (10 µM), 1 µL of template DNA, and 22 µL of ddH$_2$O.

PCR amplification conditions: pre-denature at 95° C. for 3 min; followed by 30 cycles (95° C. 30 s, 55° C. 30 s, and 72° C. 7 min); supplement and extend at 72° C. for 10 min.

The PCR product was digested with DpnI and transformed into the *E. coli* BL21(DE3) competent cells. Monoclones were selected and sent to Shanghai Sangon Biotech for sequencing. A strain with correct sequencing results was mixed with sterile glycerol and stored at −80° C. The strain was named BL21(DE3)-pET28a(+)-T317N-L386Y-S427E-A110E. The multicopper oxidase mutant expressed by this strain was named T317N-L386Y-S427E-A110E.

Example 5: Expression and Purification of Mutant T317N-L386Y-S427E

BL21(DE3)-pET28a(+)-T317N-L386Y-S427E was inoculated in LB broth containing 50 μg/ml kanamycin, and cultured at of 37° C. and 220 rpm for 10 h, a seed culture was inoculated into TB broth containing 50 μg/ml kanamycin with 2% of inoculation size, and cultured at a 37° C. and 220 rpm until $OD_{600}$ was equal to 0.6 to 0.8, then added with 0.1 mM of IPTG and 1 mM of $CuCl_2$, and induced at 20° C. and 220 rpm for 20 to 22 h. The obtained fermentation broth was centrifuged at 4° C. and 8000 r/min for 15 min, and the cells were collected, and washed twice with a 20 mM phosphate buffer of pH 7.0, and then the cells were resuspended with the phosphate buffer. The suspension was placed on ice, and the cells were disrupted by sonication (35% power, oscillating for 2 s and stopping for 4 s) until the solution was clear. The solution was centrifuged at 4° C. and 10000 r/min for 30 min and the supernatant was collected, namely, a crude enzyme solution. The crude enzyme solution was filtered through a 0.22 μm filter and purified by HisTrap FF affinity column to obtain a pure enzyme. After determining, the specific enzyme activity was 5.58 U/mg.

The recombinant bacteria BL21(DE3)-pET28a(+)-MCOB (WT), BL21(DE3)-pET28a(+)-T317N-L386Y, BL21(DE3)-pET28a(+)-T317N-L386Y-A110E and BL21(DE3)-pET28a(+)-T317N-L386Y-S427E-A110E were fermented and cultured according to the above method, and were isolated to obtain unmutated multicopper oxidase (WT) and mutant T317N-L386Y, T317N-L386Y-A110E and T317N-L386Y-S427E-A110E.

Example 6: Determination of Activity and Analysis of Enzymatic Properties of Multicopper Oxidase (1) Effect of Temperatures on Activity of Multicopper Oxidase The activities of multicopper oxidase obtained by purifying and the substrate were determined by a visible light absorptiometry at different temperatures (40, 45, 50, 55, 60 and 65° C.). The relative activity at each temperature was calculated according to 100% of the highest activity so as to determine the optimum reaction temperature of the enzyme. The results showed that the optimum reaction temperatures of WT, T317N-L386Y, T317N-L386Y-S427E, T317N-L386Y-A110E and T317N-L386Y-S427E-A110E were all 55° C.

(2) Effect of pH on Activity of Multicopper Oxidase

At an optimum temperature of 55° C., the activities of the enzyme at different pH (2.5, 3.0, 3.5, 4.0, 4.5 and 5.0) were determined by the visible light absorptiometry. The relative activity at each pH was calculated according to 100% of the highest activity so as to determine the optimum reaction pH. The results showed that the optimum reaction pH of WT, T317N-L386Y, T317N-L386Y-S427E, T317N-L386Y-A110E and T317N-L386Y-S427E-A110E were all pH 3.0, while the relative activity of T317N-L386Y, T317N-L386Y-S427E, T317N-L386Y-A110E and T317N-L386Y-S427E-A110E at pH 4.0 all increased compared with WT.

(3) Determination of Catalytic Parameters of the Multicopper Oxidase

The purified enzyme WT, T317N-L386Y, T317N-L386Y-S427E, T317N-L386Y-A110E or T317N-L386Y-S427E-A110E was mixed with citric acid-sodium citrate buffer (the citric acid-sodium citrate buffer contains ABTS and 1 mM of $CuCl_2$) to obtain the reaction system. The reaction system includes 100 μL of an enzyme solution, 2900 μL of a citric acid-sodium citrate buffer. Concentration of ABTS changed from 0.250 to 0.025 mM intervals of 0.025 mM. The reaction temperature and pH adopt the optimum temperature (55° C.) and optimum pH (3.0) of the enzyme. The activity of the multicopper oxidase was calculated by detecting the absorbance of the reaction system after enzyme reacting with the substrate for 2 min by using a reaction kinetics instrument. Furthermore, the Km, Kcat and Kcat/Km were calculated by Lineweaver-Burk plot.

The amount of enzyme required to catalyze 1 μmol of substrate per minute to oxidize is defined as an activity unit (U). As shown in Table 1, compared with WT, the Kcat/Km of T317N-L386Y-A110E decreased 0.13 times, the Kcat/Km of T317N-L386Y-S427E-A110E decreased 0.31 times, while the Kcat/Km of T317N-L386Y and T317N-L386Y-S427E increased 1.15 times and 0.95 times.

TABLE 1

Catalytic parameters of the multicopper oxidase

| Enzyme | Km (μM) | Kcat ($S^{-1}$) | Kcat/Km ($S^{-1} \cdot mM^{-1}$) | Specific activity (U/mg) |
|---|---|---|---|---|
| WT | 507.21 | 3.72 | 7.33 | 3.33 |
| T317N-L386Y | 335.35 | 5.31 | 15.83 | 5.79 |
| T317N-L386Y-S427E | 338.94 | 4.85 | 14.30 | 5.58 |
| T317N-L386Y-A110E | 534.79 | 3.40 | 6.38 | 2.84 |
| T317N-L386Y-S427E-A110E | 568.34 | 2.91 | 5.12 | 2.43 |

(4) Effect of NaCl on Activity of Multicopper Oxidase

100 μL of WT, T317N-L386Y, T317N-L386Y-S427E, T317N-L386Y-A110E and T317N-L386Y-S427E-A110E purified by HisTrap FF affinity column were placed in 2 mL of a phosphate buffer containing 3%, 6%, 9%, 12%, 15% and 18% NaCl (W/V, g/100 mL), the initial activity was determined immediately, the remaining activity was determined after being placed at a temperature of 4° C. for 1 h, and the relative activity was equal to the remaining activity divided by the initial activity. The activity was determined at 55° C. and pH 3.0. After T317N-L386Y-S427E, T317N-L386Y, T317N-L386Y-A110E, T317N-L386Y-S427E-A110E and WT were treated for 1 h in 3% NaCl (W/V), the activities were almost not lost; after T317N-L386Y-S427E, T317N-L386Y, T317N-L386Y-A110E, T317N-L386Y-S427E-A110E and WT were treated for 1 h in 6%, 9%, 12%, 15% and 18% NaCl (W/V), the remaining activity of T317N-L386Y, T317N-L386Y-A110E and T317N-L386Y-S427E-A110E did not change much compared with WT, while the remaining activity of T317N-L386Y-S427E was higher than that of WT, indicating that the salt tolerance of the mutant T317N-L386Y-S427E was improved compared with WT. (See Table 2).

TABLE 2

Effect of NaCl on activities of WT and mutants

| NaCl (%) | 3 | 6 | 9 | 12 | 15 | 18 |
|---|---|---|---|---|---|---|
| WT | 99.5% | 83.5% | 64.5% | 53.0% | 37.3% | 31.4% |
| T317N-L386Y | 98.2% | 84.0% | 63.5% | 51.0% | 35.4% | 33.2% |
| T317N-L386Y-S427E | 99.9% | 100.0% | 76.0% | 67.5% | 60.3% | 41.5% |
| T317N-L386Y-A110E | 98.1% | 82.2% | 58.0% | 48.4% | 41.5% | 29.1% |
| T317N-L386Y-S427E-A110E | 100.0% | 91.5% | 62.7% | 52.4% | 44.5% | 33.4% |

What is claimed is:

1. A multicopper oxidase mutant, wherein: (a) the multicopper oxidase mutant comprises the amino acid sequence SEQ ID NO:1, or (b) the multicopper oxidase mutant comprises the amino acid sequence SEQ ID NO:1 with residue number 110 mutated to glutamic acid (A110E), and wherein the multicopper oxidase mutant possesses oxidase enzymatic activity.

2. A method for producing a multicopper oxidase mutant comprising:

inoculating a genetically engineered bacterium transformed with a gene encoding a multicopper oxidase mutant of claim 1 into a medium;

inducing the genetically engineered bacterium to express the gene;
collecting the genetically engineered bacterium;
disrupting the genetically engineered bacterium; and
purifying the multicopper oxidase mutant from the disrupted genetically engineered bacterium.

3. The method according to claim 2, which further comprises:
adding the purified multicopper oxidase mutant to a food, thereby removing biogenic amines in the food by degradation.

4. The method according to claim 3, wherein the food comprises soy sauce.

5. The method according to claim 3, wherein the biogenic amine comprises at least one of tryptamine, phenethylamine, putrescine, cadaverine, histamine, tyramine, spermine and spermidine.

* * * * *